United States Patent [19]

Lee et al.

[11] 4,048,080

[45] Sept. 13, 1977

[54] LUBRICATING OIL COMPOSITION

[75] Inventors: Gary D. Lee; Paul F. Vartanian; Joseph B. Biasotti, all of Wappingers Falls, N.Y.

[73] Assignee: Texaco Inc., New York, N.Y.

[21] Appl. No.: 693,458

[22] Filed: June 7, 1976

[51] Int. Cl.$^2$ .................... C07D 41/00; C07D 41/06
[52] U.S. Cl. ............................ 252/51.54; 252/51.5 R
[58] Field of Search .................................. 252/51.5 A

[56] References Cited

U.S. PATENT DOCUMENTS

| 2,944,025 | 7/1960 | Verdol | 252/51.5 |
| 3,151,957 | 10/1964 | Clough et al. | 44/71 |
| 3,172,892 | 3/1965 | Le Suer et al. | 252/51.5 |
| 3,452,002 | 6/1969 | Brasch | 44/63 |

FOREIGN PATENT DOCUMENTS 1,383,423  2/1975  United Kingdom

Primary Examiner—Arthur P. Demers
Attorney, Agent, or Firm—Thomas H. Whaley; Carl G. Ries; James J. O'Loughlin

[57] ABSTRACT

A lubricating oil composition containing an amine-alkenylsuccinic acid or anhydride reaction product in which the alkenyl radical has a molecular weight ranging from about 250 to 3000.

14 Claims, No Drawings

LUBRICATING OIL COMPOSITION

BACKGROUND OF THE INVENTION

1. Field of the Invention

Dispersants for lubricating oil compositions produced by the reaction of an alkenylsuccinic acid or anhydride with an amine or polyamine are well known. These products are obtained by reacting an alkenylsuccinic acid or anhydride with the amine or polyamine under thermal conditions to produce an alkenylsuccinimide or an alkenylsuccinamic acid depending on the temperature of the reaction which effects water removal. No amine or polyamine substituent is added to the alkenyl radical in the alkenylsuccinic acid or anhydride in this reaction.

Alkenylsuccinic acids or anhydrides have also been chlorinated followed by a reaction with an amine or a polyamine under thermal reaction conditions to produce an effective dispersant. This reaction produces a reaction product in which a portion of the amine or polyamine reactant is directly attached to the alkenyl radical of the alkenylsuccinic acid or anhydride. A nitrogen to carbon linkage between the amine and the alkenyl radical takes place following the splitting off of hydrogen chloride in this process.

2. Description of the Prior Art

The prior art to which this invention relates includes the following patents, U.S. Pat. Nos: 3,219,666, 3,202,678, 3,172,892 and 3,131,150.

This application is related to application Ser. No. 693,459 filed on 06/07/76 which disclosure is incorporated in the present application.

SUMMARY OF THE INVENTION

A principal object of the present invention is to provide a lubricating oil composition containing a novel dispersant reaction product. Another object is to provide a dispersant reaction product which exhibits a higher nitrogen content than known dispersant additives.

Still another object is to provide a method for preparing a novel dispersant additive.

A further object is to provide a novel lubricating oil composition containing the amine-alkenylsuccinic acid or anhydride reaction product of the invention.

It has been found that an amine including substituted amines can be reacted with an alkenylsuccinic acid or anhydride in the presence of a free radical initiator. This reaction leads to the production of a unique reaction product designated herein as an amine-alkenylsuccinic acid or as an amine-alkenylsuccinic anhydride reaction product. When this reaction has been conducted employing certain amine or polyamine reactants, the reaction product has been found to possess a higher level of nitrogen than has heretofore been obtained in known processes using the same reactants. It is postulated that this higher nitrogen content is due to the production of a structurally unique reaction product involving the addition of a portion of the amine directly on to the alkenyl radical of the alkenylsuccinic acid or anhydride in addition to that added via imide formation. Moreover, this new structure is theorized to be a new carbon to carbon bond linkage between the amine reactant and the alkenyl radical at the site of its olefinic bond.

The amine-alkenylsuccinic acid or anhydride reaction product of the invention is effective as a dispersant in a lubricating oil composition. It is an important feature that this novel reaction product is essentially ashless, i.e., it does not form ash deposits in the crankcase zone of the engine. This feature allows the formulation of improved lubricating oil compositions which exhibit improved engine cleanliness and performance.

DESCRIPTION OF THE PREFERRED EMBODIMENTS

The novel amine-alkenylsuccinic acid or anhydride reaction product is obtained by reacting an alkenylsuccinic acid or anhydride, having the structural unit represented by the formula:

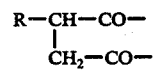

in which R is an alkenyl radical having an average molecular weight ranging from about 250 to 3,000 with an amine, represented by the formula:

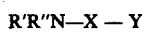

in which R' and R" represent hydrogen or a monovalent alkyl, aminoalkyl or hydroxyalkyl radical having from 1 to 8 carbon atoms, X is a divalent hydrocarbon radical having from 2 to 8 carbon atoms and Y is a radical, selected from the group consisting of hydrogen, amino, hydroxy and a radical having the formula $O(R'''O)_xH$ in which R''' is an alkylene radical having from 2 to 3 carbon atoms an x is an integer from 1 to 5, in the presence of a free-radical initiator using a molar proportion of said amine to said alkenylsuccinic acid or anhydride greater than 1.

The alkenyl radical on the alkenylsuccinic acid or anhydride reactant has an average molecular weight ranging from about 250 to 3,000 as determined by the ASTM Method D-2503. A preferred alkenylsuccinic acid or anhydride starting reactant is one in which the alkenyl radical has an average molecular weight ranging from about 500 to 2,000 with the particularly preferred species having a molecular weight ranging from about 750 to 1,500.

The alkenyl radical on the alkenylsuccinic acid or anhydride reactant is obtained in the polymerization of a monoolefin according to known methods. Thus, monoolefins having from 2 to 6 carbon atoms, such as ethylene, propylene 1-butene, 2-butene, isobutylene, amylene, hexylene and mixtures thereof are polymerized to produce monoolefinic polymers or copolymers having an appropriate average molecular weight according to known methods. The monoolefinic polymer or copolymer is then reacted with maleic anhydride to produce the alkenylsuccinic acid or anhydride reactant employed in the production of the reaction product of this invention. The procedures referred to are well known in the art and the processes involved do not constitute any part of the present invention.

The amine reactant employed to produce the reaction product of the invention is represented by the formula:

in which R' and R" represent hydrogen or a monovalent alkyl, aminoalkyl or hydroxyalkyl radical having from 1 to 8 carbon atoms, X is a divalent hydrocarbon radical having from 2 to 8 carbon atoms and Y is a radical, selected from the group consisting of hydrogen, amino, hydroxy and a radical having the formula O(R'''O)$_x$H in which R''' is an alkylene radical having from 2 to 3 carbon atoms and $x$ is an integer from 1 to 5.

Monoamines which can be employed to produce the reaction product of the invention include ethylamine, propylamine, butylamine, dimethylamine and diethylamine. The preferred monoamines are the alkyl and dialkyl monoamines having from 1 to about 6 carbon atoms.

Polyamines which can be employed as the amine reactant include the alkylene polyamines, such as ethylenediamine, propylene diamine, butylamine diamine, diethylaminetriamine, triethylenetetramine, tetraethylenepentamine, pentaethylenehexamine, dipropylenetriamine, trimethylenediamine, tetramethylenediamine, pentamethylenediamine, hexamethylenediamine and the like.

The amine reactant for producing the reaction product of the invention may also be a substituted amine reactant. Hydroxy-substituted amine which can be employed include ethanolamine, propanolamine, butanolamine, diethanolamine and the like.

In preparing the reaction product of the invention, the molar proportion of the amine reactant to the alkenylsuccinic acid or anhydride reactant employed is greater than 1. A preferred molar proportion of the amine to the alkenylsuccinic acid or anhydride are proportions in the range from about 1.5 to 10 moles of amine per mole of alkenylsuccinic acid or anhydride. It is particularly preferred to employ a molar proportion ranging from about 2 to 5 moles of amine per mole of the alkenylsuccinic acid or anhydride.

The present process for the production of a novel amine-alkenylsuccinic acid or anhydride reaction product is conducted in the presence of conventional initiator which decomposes to form free radicals. Suitable initiators include the organic peroxides, for example the dialkyl peroxides, the azo, and the diazol compounds. Highly effective initiators include azobisisobutyronitrile, benzoyl peroxide, di-t-butyl peroxide, isopropyl peroxy carbonate, t-butyl peroxy isopropyl carbonate and t-butyl perbenzoate.

The free radical initiator is employed in a proportion ranging from about 0.1 to 2.0 weight percent of the initiator based on said alkenylsuccinic acid or anhydride. The preferred concentration of the free-radical initiator is from about 0.50 to about 1.25 weight percent.

EXAMPLE I 100 grams (0.053 mole base on active anhydride) of polyisolutenylsuccinic anhydride in which the polyisobutenyl radical has an average molecular weight of 1290, 15 grams (0.25 mole) of ethylenediamine and 1.0 grams of azobisisobutyronitrile are added to a reactor and heated with stirring to 90° C under a nitrogen atmosphere. These reaction conditions are maintained for three hours. The reactor is then set up for distillation. Most of the excess amine is removed by elevating the temperature to 130° C and using a nitrogen purge. The reaction product is cooled to room temperature, dissolved in 100 milliliters of hexane and twice washed with 100 milliliters of 90% aqueous methanol. The hexane solvent is removed at 90° C using reduced pressure to yield 93 grams of the reaction product. This reaction product has the following analysis. % N = 1.7.

EXAMPLE II 1,100 grams (0.59 mole) polyisobutenylsuccinic anhydride in which the polyisobutenyl has an average molecular weight of 1,290, 165 grams (2.75 moles) of ethylenediamine and 11 grams of azobisisobutyronitrile are charged to a reactor and reacted as in Example I above.

1,000 grams of a reaction product are recovered having the following analysis. % N = 1.6.

EXAMPLE III 110 grams (0.059 mole) polyisobutenylsuccinic anhydride in which the polyisobutenyl radical has an average molecular weight of 1290. 16.50 grams (0.275 mole) of ethylenediamine and 1.1 grams of t-butylperoxy isopropylcarbonate are charged to a reactor and reacted as in Example I above.

100 grams of a reaction product are recovered having the following analysis. % N = 1.5.

EXAMPLE IV 1,100 grams (0.59 mole) polyisobutenylsuccinic anhydride in which the polyisobutenyl radical has an average molecular weight of 1290, 510 grams (2.7 moles) tetraethylenepentamine and 5.5 grams azobisisobutyronitrile are charged to a reactor and reacted as in Example I above.

1,120 grams of a reaction product are recovered having the following analysis: % N = 3.56.

EXAMPLE V 3,000 grams (1.63 moles) polyisobutenylsuccinic anhydride in which the polyisobutenyl radical has an average molecular weight of 1290, 752 grams (7.3 moles) diethylenetriamine and 30 grams azobisisobutyronitrile are charged to a reactor and reacted as in Example I above.

3100 grams of a reaction product are recovered having the following analysis: % N = 2.92.

EXAMPLE VI (Thermal process)

500 grams (0.27 mole) of polyisobutenylsuccinic anhydride in which the polyisobutenyl radical has an average molecular weight of 1,290, 125 grams (1.21 moles) diethylenetriamine are charged to a reactor and reacted as in Example I above.

490 grams of a reaction product are recovered having the following analysis: % N = 1.81.

EXAMPLE VII (Thermal Process)

100 grams (0.053 mole) of polyisobutenylsuccinic anhydride in which the polyisobutenyl radical has an average molecular weight of 1,290, and 15 grams (0.25 mole) of ethylenediamine are charged to a reactor and reacted as in Example I above.

94 grams of a reaction product are recovered having the following analysis: % N = 1.40.

EXAMPLE VIII 100 grams (0.053 mole) polyisobutenylsuccinic anhydride in which the polyisobutenyl radical has an average molecular weight of 1,290, 15 grams (0.25 mole) of ethylenediamine and 0.75 gram of azobisisobutyronitrile are charged to a reactor and heated with stirring to 90° C. These reaction conditions are maintained for three hours. The reaction product is cooled to room temperature, dissolved in 100 milliliters of hexane and twice washed with 100 milliliters of 90% aqueous methanol. The hexane solvent is evaporated off by heating under a nitrogen stream to yield the reaction product. This reaction product has the following anaylsis: % N = 1.7.

EXAMPLE IX 100 grams (0.071 mole) polyisobutenylsuccinic anhydride in which the polyisobutenyl radical has an average molecular weight of 750, 15 grams (0.25 mole) of ethylenediamine and 1 gram of azobisisobutyronitrile are charged to a reactor and reacted as in Example VIII above.

98 grams of a reaction product are recovered having the following analysis: % N = 2.17.

EXAMPLE X 100 grams (0.053 mole) polyisobutenylsuccinic anhydride in which the polyisobutenyl radical has an average molecular weight of 1,290, 15 grams (0.147 mole) of N,N-dimethylpropane-1,3-diamine and 1 gram of azobisisobuteronitrile are charged to a reactor and reacted as in Example VIII above.

108 grams of a reaction product are recovered having the following analysis: % N = 1.60.

EXAMPLE XI 100 grams (0.053 mole) polyisobutylenesuccinic anhydride in which the polyisobutenyl radical has an average molecular weight of 1290, 25 grams (0.098 mole) ethoxylated ethylenediamine in which an average of four ethylene oxide radicals have reacted with each ethylenediamine, and 1 gram of azobisisobutyronitrile are charged and reacted as in Example VIII above.

115 grams of a reaction product are recovered having the following analysis. % N = 2.2.

EXAMPLE XII 3,000 grams (1.63 moles) of polyisobutenylsuccinic anhydride in which the polyisobutenyl radical has an average molecular weight of 1,290, 752 grams (7.3 moles) diethylenetriamine and 15 grams azobisisobutyronitrile are charged to a reactor and heated with stirring to 90° C. These conditions are maintained for three hours. The excess diethylenetriamine and other volatile components are then removed at 150° C using reduced pressure.

3100 grams of a reaction product are recovered having the following analysis. % N = 2.44.

EXAMPLE XIII 3,000 grams (1.63 moles) of polyisobutenylsuccinic anhydride in which the polyisobutenyl radical has an average molecular weight of 1290, 450 grams (7.5 moles) ethylenediamine and 15 grams of azobisisobutyronitrile are charged to a reactor and heated with stirring to 90° C. The conditions are maintained for 3 hours. The excess ethylenediamine and other volatile components are then removed at 130° C using reduced pressure.

3080 grams of the reaction product are recovered having the following analysis. % N = 1.86.

The novel dispersant additive of the invention is effectively employed in an oil of lubricating viscosity. This oil substrate may be a mineral, a synthetic or a mixed mineral-synthetic lubricating oil. Suitable synthetic oil substrates include ester base oils, alkylene polymers, alkylene epoxide type polymers, alkyl benzenes, polyphenyls and the like.

It is preferred to employ the dispersant additive in a hydrocarbon mineral oil. This oil substrate can be a paraffin base, naphthenate base, or mixed paraffinnaphthene constituting from about 85 to 95 percent of the lubricant composition. The lubricating oil base will generally have been subjected to solvent refining to improve its lubricity and viscosity temperature relationship as well as solvent dewaxing to remove waxy components and improve the pour of the oil. Generally, mineral lubricating oils having an SUS viscosity at 100° F between 50 and 100 may be used in the formulation of the improved lubricants of this invention although the preferred viscosity range will be from between 70 and 300 SUS at 100° F. A blend of mineral base oils can be employed to provide a suitable base oil for either a single or multi-grade motor oil.

The dispersant additive of the invention was tested for its effectiveness in mineral lubricating oil compositions in the Bench V-C Test and in the Sequence V-C Test.

The Bench V-C Test is conducted by heating the test oil mixed with a synthetic hydrocarbon blowby and a diluent oil at a fixed temperature for a fixed time period. After heating, the turbidity of the resultant mixture is measured. A low % turbidity (0–10) are indicative of good dispersancy while high results (20–100) are indicative of oils increasingly poor dispersancy.

The Sequence V-C Test is detailed in the ASTM Special Technical Publication under 315-F. This procedure is used to evaluate crankcase motor oils wih respect to sludge and varnish deposits as well as their ability to keep the positive crankcase ventilation (PCV) valve clean and functioning properly. Ratings of 0 to 10 are given, 10 representing absolutely clean and 0 rating representing heavy sludge and varnish deposits.

Composition A was prepared from a mineral oil base that when mixed with other additives afforded a multi-grade SAE-10W40 motor oil composition. The mineral oil base used had the following inspection values:

| Viscosity 100° F | (SUS) 210° F | Viscosity Index | Specific Gravity | Ash | Pour Point (° F) | % S |
|---|---|---|---|---|---|---|
| 131 | 42 | 98 | 0.8665 | 0.001 | .0 | 0.14 |

Based on the weight of the fully formulated lubricating oil composition including the dispersant, composition A also contained 0.23% calcium as a calcium carbonate overbased calcium sulfonate, 0.15% zinc from a dithiophosphate made from heptanol and isopropylalcohol, 0.25% dioctyldiphenylamine, 10% of an oil solution of an ethylene-propylene copolymer of 20,000 to 50,000 molecular weight and 0.5% of a polyester type methacrylate copolymer.

Composition B was prepared from two solvent-neutral-mineral oil (SNO) bases to provide a single SAE 30 grade motor oil composition. The mineral oil bases used SNO-20 and SNO-40 in about a 4.5 to 1 weight ratio, respectively. The mineral oil bases had the following inspection values:

| Oil Base | Viscosity (SUS) 100° F | 210° F | Viscosity Index | Specific Gravity | Ash | Pour Point ° F | % S |
|---|---|---|---|---|---|---|---|
| SNO-20 | 335 | 53.5 | 95 | 0.8816 | 0.002 | +10 | 0.29 |
| SNO-40 | 850 | 77.5 | 88 | 0.8939 | 0.002 | +15 | 0.40 |

Based on the weight of the fully formulated composition, Composition B also contained 0.23% calcium as calcium carbonate overbased calcium sulfonate, 0.15% zinc from a dithiophosphate made from heptanol and isopropyl alcohol, 0.25% dioctyldiphenylamine, 0.05% of a polymethacrylate pour depressant and 150 parts per million of a dimethylsilicone anti-foamant.

The effectiveness of the lubricating oil compositions of the invention are shown in the following test results:

| BENCH V-C TEST (OIL COMPOSITION A) | | |
|---|---|---|
| Product | Weight % Product | Bench V-C Test |
| Example I | 3.0 | 3.5 |
| Example II | 3.0 | 3.5 |
| Example III | 3.0 | 3.5 |
| Example IV | 3.0 | 4.0 |
| Example V | 3.0 | 3.0 |
| Example VII (Thermal) | 3.0 | 10.5 |
| Example VIII | 3.0 | 9.0 |
| Example XIII | 3.0 | 6.0 |

| SEQUENCE V-C TEST (OIL COMPOSITION B) | | | | |
|---|---|---|---|---|
| | | Sequence V-C Test[a] | | |
| Product | Weight % Product | S. | Av. | Pv. |
| Example II | 4.0 | 9.7 | 8.0 | 8.2 |
| Example XII | 3.8 | 9.7 | 7.8 | 8.2 |
| Example XIII | 4.0 | 9.5 | 7.8 | 8.6 |

[a]The ratings indicated are: S-total sludge, AV-average varnish, and PV-piston varnish,; the minimum limits for SE-quality oil are 8.5, 8.0 and 7.9, respectively.

The foregoing tests show that the oil composition of the invention containing the novel amine-alkenylsuccinic acid or anhydride reaction product as the dispersant additive meets the sludge and varnish requirements for an effective motor oil composition.

We claim:
1. A lubricating oil composition comprising a major proportion of a base oil of lubricating viscosity and a minor dispersant amount of a reaction product prepared by the process which comprises reacting an alkenyl succinic acid or anhydride having the structural unit represented by the formula:

$$\begin{array}{l} R-CH-CO- \\ \phantom{R-}| \\ \phantom{R-}CH_2-CO- \end{array}$$

in which R is an alkenyl radical having a molecular weight ranging from about 250 to 3000 with an amine represented by the formula:

$$R'R''N - X - Y$$

in which R' and R" represent hydrogen or a monovalent alkyl, aminoalkyl or hydroxyalkyl radical having from 1 to 8 carbon atoms, X is a divalent hydrocarbon radical having from 2 to 8 carbon atoms and Y is radical selected from the group consisting of hydrogen, amino, hydroxyl and a radical having the formula $O(R'''O)_xH$ in which R''' is an alkylene radical having from 2 to 3 carbon atoms and x is an integer from 1 to 5, in the presence of a free radical initiator, the molar proportion of said amine to said succinic acid or anhydride being greater than one.

2. A lubricating oil composition according to claim 1, in which said alkenyl radical is a mono-olefinic radical derived from the polymerization of an olefin having from two to six carbon atoms.

3. A lubricating oil composition according to claim 1, in which the alkenyl radical in said alkenyl succinic compound has a molecular weight ranging from about 500 to 2,000.

4. A lubricating oil composition according to claim 1, in which the alkenyl radical in said alkenyl succinic compound has a molecular weight ranging from about 750 to 1,500.

5. A lubricating oil composition according to claim 1, in which said alkenyl succinic compound is a polyisobutenyl succinic anhydride.

6. A lubricating oil composition according to claim 1, in which said alkenylsuccinic compound is a polypropenylsuccinic anhydride.

7. A lubricating oil composition according to claim 1, in which the molar proportion of said amine to said alkenylsuccinic acid or anhydride is at least about 1.5 to 10.

8. A lubricating oil composition according to claim 1, in which the molar proportion of said amine to said alkenylsuccinic acid or an anhydride is from about 2 to 5.

9. A lubricating oil composition according to claim 1, in which said free radical initiator is selected from the group consisting of organic peroxides, azo and diazo compounds.

10. A lubricating oil composition according to claim 1, in which the alkenyl radical in said alkenyl succinic compound is polyisobutenyl having an average molecular weight ranging from 1050 to 1400.

11. A lubricating oil composition according to claim 1, in which said amine is diethylenetriamine.

12. A lubricating oil composition according to claim 1, in which said amine is tetraethylenepentamine.

13. A lubricating oil composition according to claim 1, in which said base oil consists of from about 85 to 95 weight percent of said composition.

14. A lubricating oil composition comprising a major proportion of a base oil of lubricating viscosity and a minor dispersant amount of a reaction product prepared by the process which comprises reacting an alkenyl succinic acid or anhydride having the structural unit represented by the formula:

$$\begin{array}{l} R-CH-CO- \\ \phantom{R-}| \\ \phantom{R-}CH_2-CO- \end{array}$$

in which R is an alkenyl radical having a molecular weight ranging from about 250 to 3,000 with ethylenediamine in the presence of a free radical initiator, the molar proportion of said ethylenediamine to said succinic acid or anhydride being greater than one.

* * * * *